United States Patent
Abrahamson et al.

(10) Patent No.: US 8,433,385 B2
(45) Date of Patent: Apr. 30, 2013

(54) IMPLANTABLE MEDICAL DEVICE

(75) Inventors: Hans Abrahamson, Stockholm (SE);
Anders Björling, Solna (SE); Tomas Snitting, Stockholm (SE); Nils Holmström, Järfälla (SE)

(73) Assignee: St. Jude Medical AB, Jarfalla (SE)

( * ) Notice: Subject to any disclaimer, the term of this patent is extended or adjusted under 35 U.S.C. 154(b) by 453 days.

(21) Appl. No.: 12/809,304

(22) Filed: Jun. 18, 2010

(65) Prior Publication Data

US 2010/0292550 A1    Nov. 18, 2010

(51) Int. Cl.
*A61B 5/05* (2006.01)

(52) U.S. Cl.
USPC ........... 600/345; 600/347; 600/373; 600/505; 600/506

(58) Field of Classification Search ............ None
See application file for complete search history.

(56) References Cited

U.S. PATENT DOCUMENTS

| | | | |
|---|---|---|---|
| 6,517,482 B1 | 2/2003 | Elden et al. | |
| 6,841,389 B2 | 1/2005 | Novikov et al. | |
| 7,164,947 B2 | 1/2007 | Holmström et al. | |
| 7,200,442 B1 * | 4/2007 | Koh et al. | 607/28 |
| 2001/0021864 A1 | 9/2001 | Molin | |
| 2003/0176807 A1 * | 9/2003 | Goetz et al. | 600/547 |
| 2004/0127780 A1 | 7/2004 | Ollmar et al. | |
| 2007/0156061 A1 * | 7/2007 | Hess | 600/547 |
| 2007/0161881 A1 * | 7/2007 | Ollmar et al. | 600/347 |
| 2009/0093857 A1 * | 4/2009 | Markowitz et al. | 607/11 |

OTHER PUBLICATIONS

High Frequency Impedance Analyzer HP4291A.*
Fu, et al., Reagentless Immunosensing Assay via Electrochemical Impedance for Hepatitis B Surface Antigen Monitoring Based on Polypyrrole and Gold Nanoparticles as Matrices, Chinese Journal of Chemistry, 2006, 24, 59-64.*

* cited by examiner

*Primary Examiner* — Michael Kahelin
*Assistant Examiner* — Mitchell Alter

(57) ABSTRACT

An analyte measuring system has an implantable medical device having a signal source arranged for generating a current signal and electrodes for applying the current signal to a surrounding tissue in a subject body. The device measures a resulting voltage signal with the electrodes and calculates an impedance signal therefrom. The system comprises a signal processor arranged for generating an estimate of a concentration of an analyte in the tissue based on a spectrum analysis of the determined impedance signal.

11 Claims, 6 Drawing Sheets

IMPLANTABLE MEDICAL DEVICE

BACKGROUND OF THE INVENTION

1. Field of the Invention

The present invention generally relates to implantable medical devices, and in particular to such devices capable of estimating analyte concentration in a subject body.

2. Description of the Prior Art

There is a great need in measuring different analytes in the animal and human body for diagnostic and medical purposes. Today, such analyte measurements are most often performed on blood samples taken from the subjects and analyzed in a laboratory environment. Although drawing a test sample of blood may be simple, it affects the subject's quality of life as he or she must often visit a healthcare facility for taking the sample. In addition, the equipment needed for analysis may be limited to hospital environments. As a consequence, some subjects must therefore make visits to the hospitals on a regular basis.

Several portable sensors implantable in the subject body or at least worn by the subject have been presented. Such sensors are most often based on the local measurement of an analyte in the immediate vicinity of the sensor or even in a measuring chamber of the sensor, through which blood flows. However, such implantable sensors often have significantly limited operational time. A major reason is the formation of connective tissue around the sensor or the measuring chamber. This connective tissue layer prevents or at least severely limits the transport of the analyte close to the sensor. As a consequence, these sensors therefore often become inoperable or highly unpredictable even after a very short operational period.

United States Patent Application Publication Nos. 2004/0127780 and 2004/0161881 and U.S. Pat. Nos. 6,841,389 and 6,517,482 disclose non-invasive determination of a substance, typically glucose, in blood of a subject. An electrical conducting probe is placed tight against a skin surface of the subject. Electric current is applied to the skin and underlying tissue using two electrodes of the probe. A resulting voltage is measured by the same or different probe electrodes. An impedance of the skin tissue can then be calculated based on the measurements and used for determining the blood glucose level in the subject.

Such a probe-based glucose measuring provides significant advantages to the subject by relaxing the need for taking blood samples, possibly at regular intervals, especially for a diabetic subject.

SUMMARY OF THE INVENTION

The prior art arrangements still have disadvantages in that continuous or regular measurements requires a visiting of the subject to a healthcare facility housing the probe and its connected signal processing computer or the patient has to be at home if having a home-installed arrangement. This will affect the life of the subject, who must in detail plan his/her whereabouts according to the assigned measuring schedule. The present invention overcomes these and other drawbacks of the prior art arrangements.

It is a general object of the present invention to provide an analyte measuring system using impedance signals for analyte concentration monitoring.

It is another object of the invention to provide such a system comprising an implantable medical device for determining an impedance signal indicative of an analyte concentration.

Briefly, the present invention involves an analyte measuring system having an implantable medical device, such as a pacemaker, defibrillator or cardioverter. The device contains a signal source arranged for generating a current/voltage signal having a defined frequency or frequency bandwidth. The implantable medical device is connected to two electrodes employed for applying the generated current/voltage signal to a surrounding tissue. The same or different electrodes sense a resulting voltage/current signal from the tissue.

An impedance determiner is implemented in the medical device for calculating an impedance signal based on the measured voltage/current signal and the applied current/voltage signal. The presence of an analyte will modulate the impedance signal in the frequency domain, causing a change in amplitude and/or phase depending on variations in the analyte concentration in the tissue. A signal processor is provided for performing a spectral analysis of the determined impedance signal to generate an estimate of a concentration of the analyte in the tissue.

The signal source can be a frequency tunable source for sweeping the frequency of the generated current or voltage signal over a selected frequency range. The resulting frequency varying voltage or current signal is sensed and utilized together with the applied signal for determining an impedance spectrum over the frequency range. The signal processor then estimates the analyte concentration by analyzing selected portion of the impedance spectrum.

Alternatively, the signal source applies a composite current or voltage signal having multiple different frequency components, i.e. a selected bandwidth. A resulting composite voltage or current signal is then sensed over two electrodes. The sensed voltage or current signal or the impedance signal calculated therefrom is preferably input to a set of filters for thereby get the impedance signal at selected frequencies that are analyzed by the signal processor.

The present invention is based on the finding that different chemical substances have different resonance and absorbance frequencies, which causes a modulation of the impedance signal to form different tops and dips in an absorbance frequency spectrum. By analyzing the amplitude and/or phase changes at a given frequency or preferably at multiple frequencies, the signal processor can determine absolute or relative analyte concentration estimates.

The current-voltage signal application and sensing of the present invention are preferably performed at multiple different time instances to obtain a trending in the analyte concentration. This concentration trending is of highly diagnostic value for physicians and can be used for detecting the onset, relapse or recovery from medical conditions and/or be used for medication purposes.

In a particular embodiment, the application of the current signal is synchronized to specified phases in intrinsic body activity, such as in a selected phase of a respiration cycle or heart cycle. Furthermore, synchronization of signal application can instead be, or as a complement, performed based on body posture of a subject. This synchronization reduces variability and blurring in the impedance signal, where such signal variations are due to the intrinsic body activity and/or body posture. This reduces background noise in the spectrum analysis to thereby improve the accuracy in concentration estimation.

In another particular embodiment, the implantable medical device utilizes different impedance vectors for thereby providing multiple impedance signals measured close in time. A combined processing of these impedance signals from the different impedance vectors further reduces noise and improves the processing of the impedance signal to increase the accuracy in the concentration estimation.

The invention offers the following advantages:
- Acquires measurement of blood and tissue constituents without drawing blood from patients;
- Acquires HF metrics based on known clinical measurements;
- Can be used for myocardial ischemia detection, including silent ischemia; and
- Provides an aid in determining drug dosages.

Other advantages offered by the present invention will be appreciated upon reading of the below description of the embodiments of the invention.

DESCRIPTION OF THE PREFERRED EMBODIMENTS

Figure 1:
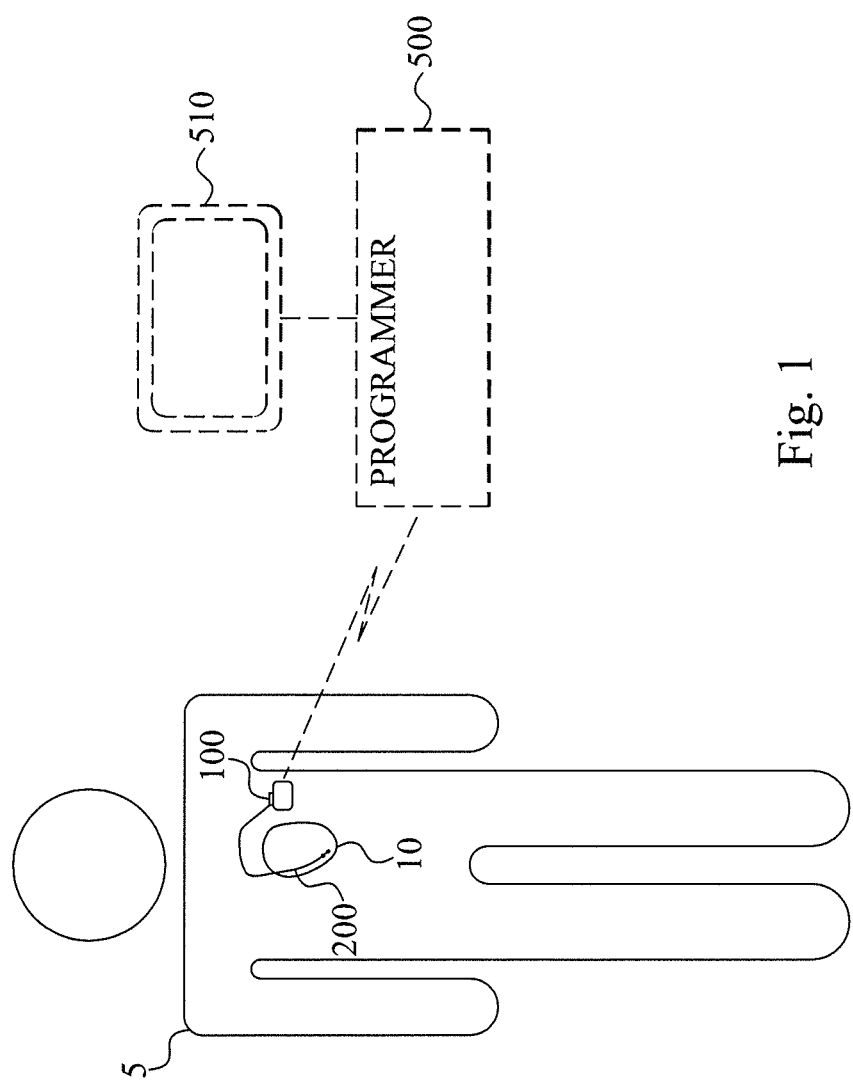
FIG. 1 is an overview of a subject equipped with an implantable medical device according to the present invention and an external communications unit adapted for wireless communication with the implantable medical device.

Throughout the drawings, the same reference characters will be used for corresponding or similar elements.

The present invention relates to measuring of analytes and different chemical substances in a human or animal body using an analyte measuring system that comprises an implantable medical device (IMD). The key concept of the invention is to base the analyte concentration estimation on impedance spectral analysis to thereby detect concentration changes of analytes of interest.

The present invention will be a valuable tool in diagnosis and evaluation of subjects having implantable medical devices and can be used as a complement to or instead of traditionally blood sampling analysis. The invention has the potential of being, in real time or close to real time, able to detect sudden changes in analyte concentration in the subject. If the monitored analyte is closely related to a medical condition, an early detection of a severe medical condition is possible even though the subject is not visiting a healthcare facility. Furthermore, by being implemented into the subject, the system of the invention can be utilized for continuous or regular analyte monitoring over time, without the need for a multitude of hospital visits.

The invention is based on the finding that an impedance-based analyte monitoring has several advantages over the enzymatic and optical techniques traditionally utilized by implantable sensors. The present invention will, thus, operate effectively over extensive periods of time even if connective tissue is growing around the IMD and its implantable electrodes. The system of the invention therefore does not need to have uninterrupted connection between the electrodes and the tissue, where analyte monitoring is performed, as the prior art solutions must.

FIG. 1 is a schematic overview of a subject 5 equipped with an IMD 100 connected to the subject's heart 10. The IMD 100 is illustrated as a device that monitors and/or provides therapy to the heart 10 of the patient 5, such as a pacemaker, defibrillator or cardioverter. The IMD 100 is connectable to at least one medical lead 200, such as intracardiac or endocardiac lead, connected to the heart 10. The medical lead 200 has electrodes in connection with its distal end connected or anchored in the heart 10. These electrodes are employed by the IMD 100 for generating the impedance signal utilized in the analyte monitoring of the invention.

In FIG. 1, the IMD 100 has been illustrated as an implantable medical device providing therapy and diagnosis to the heart 10 in the patient 5. However, the present invention is not limited thereto. In clear contrast the analyte measuring system can comprise other forms of implantable devices having access to at least two implantable electrodes. Examples of such devices include implantable drug pumps, neurological stimulators, physical signal recorders, oxygen sensors, or the like.

FIG. 1 also illustrates an external programmer or clinician's workstation 500 that can communicate with the IMD 100. As is well known in the art, such a programmer 500 can be employed for transmitting IMD programming commands causing a reprogramming of different operation parameters and modes of the IMD 100. Furthermore, the IMD 100 can upload diagnostic data descriptive of different medical parameters or device operation parameters collected by the IMD 100. Such uploaded data may optionally be further processed in the programmer 500 before display to a clinician on a connected display screen 510. In accordance with the present invention, such diagnostic data can include analyte estimations generated by the IMD 100 and/or other raw or partly processed (impedance) data relating to such analyte estimations. As is further disclosed herein, the programmer 500 or some other external device can constitute one of the units in the analyte measuring system of the invention.

Figure 2:
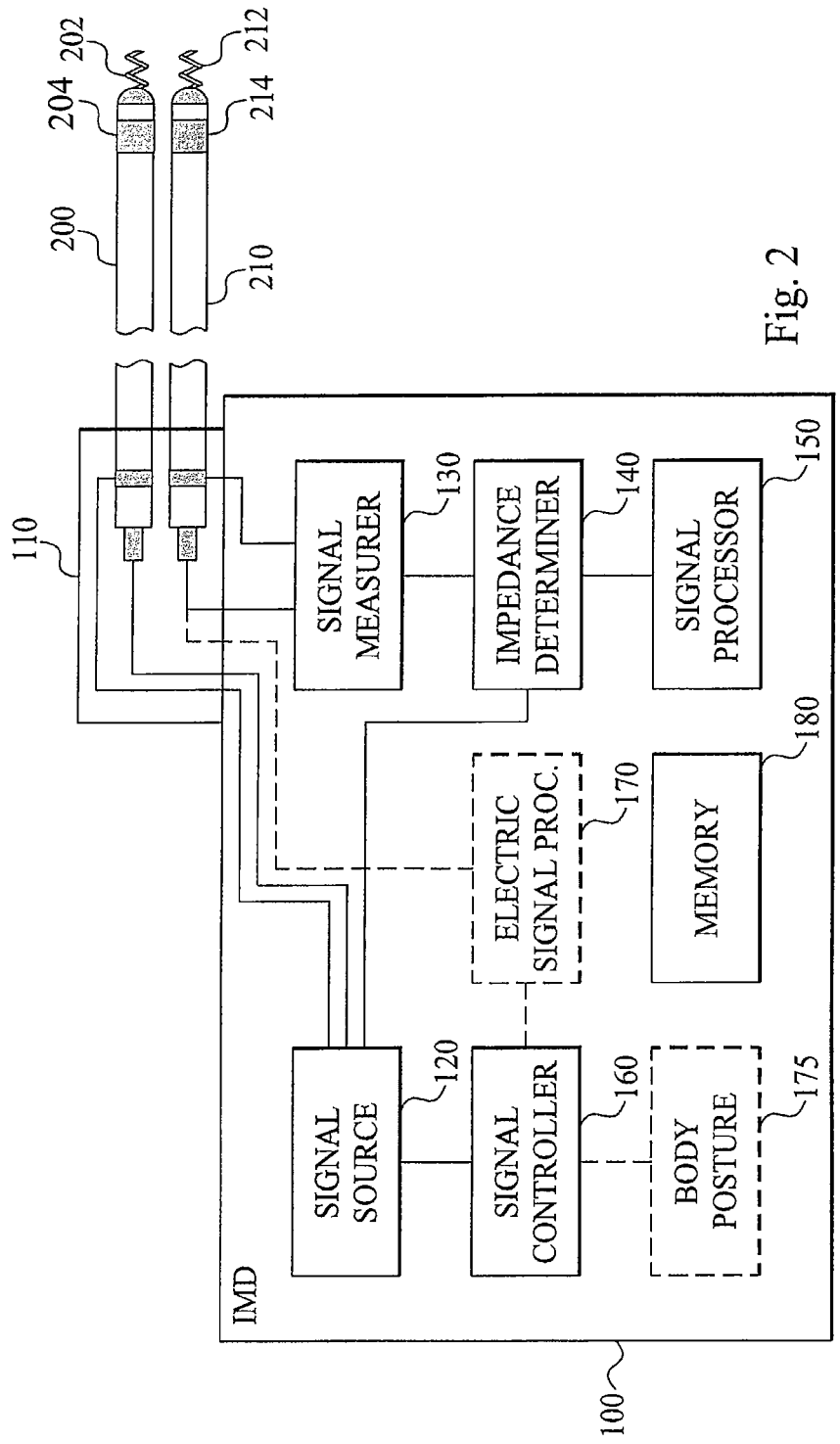
FIG. 2 is a schematic block diagram of an embodiment of an implantable medical device according to the present invention.

FIG. 2 is a schematic block diagram of an embodiment of an implantable medical device 100 according to the present invention. In this embodiment, the IMD 100 is connected to at least two implantable electrodes 202, 204; 212, 214 used for applying and sensing electric signals to and from a tissue, where analyte monitoring is desired. These electrodes 202, 204; 212, 214 are preferably arranged on one or more implantable medical leads 200; 210 connected to the IMD 100 through an electrode or lead connecting arrangement 110. As is well known in the art, such an implantable lead or catheter 200; 210 has a proximal end connected to the IMD 100 through the connecting arrangement 100. This IMD-connecting end presents one or more electric terminals that are in electric connection with the electrodes 202, 204; 212, 214 present on the opposite distal lead end, where the electric connection is achieved by electric conductors running along the length of the lead body. The distal lead end with its electrodes 202, 204; 212, 214 is then provided in connection with a tissue, preferably a heart tissue. For this purpose, the lead 200; 210 can include a tissue anchoring element, such as a helical fixation element 202; 212 illustrated in the figure, though other fixation elements, such as passive fixation elements, including fines, tines, etc., are also common. The fixation element 202; 212 can indeed constitute one of the electrodes of the lead 200; 210, while remaining electrodes 204; 214 can be ring electrodes (indifferent electrodes), tip electrodes, defibrillation electrode, or the like.

The IMD 100 can be connected to a single medical lead 200, then preferably having at least two electrodes 202, 204, such as ring electrode 204 and tip/helix electrode 202. Alternatively, the IMD 100 is connected to multiple, i.e. at least two, implantable leads 200, 210 having electrodes 202, 204; 212, 214. In either case, the at least one lead 200; 210 can be an intracardiac lead positioned in any of the chambers of the heart, such as right and/or left atrium and/or ventricle. Alternatively, the at least one lead 200; 210 could be epicardially positioned relative the heart. Also a combination of intracardial and epicardial leads is encompassed by the present invention.

One of the electrodes utilized in the signal application and sensing of the present invention could be the can or case of the IMD 100. Thus, the present invention is not limited to lead-implemented electrodes 202, 204; 212, 214.

The applying and sensing electrodes 202, 204; 212, 214 of the invention can also be used by the IMD 100 for other purposes, such as for providing stimulating pulses, cardioversion pulses, defibrillation shocks and/or sensing electrical signal from the heart.

The IMD 100 has a signal source 120, preferably a frequency tunable signal source. This signal source 120 is connected to two electrodes 202, 204; 212, 214 through the electrode connecting arrangement 110. In the illustrated implementation example, this connection is realized through the electrode connector 110 and the medical lead(s) 200, 210 in which the electrodes 202, 204; 212, 214 are provided.

The signal source 120 is arranged for generating a current or voltage signal of selected frequency (bandwidth). The signal is preferably an alternative current signal having a particular bandwidth or frequency selected based on the particular analyte to measure or monitor. The signal frequency could be a single frequency. In such a case, the signal source 120 is preferably adapted for varying the single frequency of the current or voltage signal to generate multiple such signals covering a broader frequency range. In other embodiments, the generated signal has a defined bandwidth selected by the signal source 120, such as covering from a starting frequency $f_S$ to an end frequency $f_E$. In this case, the generated current or voltage signal is a composite signal consisting of multiple frequency components. The need for varying the frequency (bandwidth) of the current/voltage signal can be somewhat relaxed as it may be possible that the generated signal has a bandwidth broad enough to cover an interesting measuring range.

In a preferred embodiment, the bandwidth or the single signal frequency is selected to be in the range of from about 1 Hz to about 1 THz. This large frequency range covers spectral changes due to the presence of several analytes that can be of interest for diagnostic and medical purposes. In most practical implementations, the bandwidth could be in the more limited interval from about 1 kHz to about 1 THz or more preferably from about 1 MHz to about 1 THz.

Below follows a short listing of several interesting analytes that can be detected by an IMD 100 or different IMDs 100 according to the invention. The listing should, though, merely be interpreted as containing preferred analyte examples and the present invention is not limited thereto.

Vitamin K

Vitamin K is involved in the coagulation of blood. More or less all patients suffering from or having been diagnosed for atrial fibrillation (AF) are on some type drug with of anticoagulatnic effects, e.g. Warfarin or other vitamin K antagonist. These drugs inhibit the synthesis of biologically active forms of the vitamin K-dependent clotting factors: II, VII, IX and X, as well as the regulatory factors protein C, protein S and protein Z. Other proteins not involved in blood clotting, such as osteocalcin, or matrix Gla protein, may also be affected.

Warfarin is very difficult to dose correctly. Patients must usually take blood samples 1-2 times a week to set the correct dosage. The present invention therefore advantageously can be used for monitoring the vitamin K concentration in a subject having an implantable medical device, such as an AF patient. The need for regular blood sampling is then relaxed and the invention can instead provide a regular and periodic monitoring of the vitamin K concentration in the subject body.

Cholesterol and Blood Fat

Many patients having IMDs such as pacemakers, defibrillators or cardioverters have high blood cholesterol, which is a risk factor for atherosclerosis, principal cause of coronary artery disease (CAD). The IMD of the invention can therefore advantageously be used for monitoring changes in blood cholesterol and blood fats through the impedance measurements of the invention.

Glucose

One of the most common comorbidities of heart failure (HF) patients is diabetes mellitus. For these patients, monitoring the blood glucose value is very important. Currently, the goal for diabetes treatment is to avoid hyper- and hypoglycemia. This is done by lifestyle changes (change of diet, increased exercise etc.) and in some cases insulin. It can be difficult to give right dosage of insulin, and blood tests are needed. The present invention can provide a significant improvement in patient's quality of life by being able to track the glucose level through the impedance measurements of the implantable medical device.

The present invention is, though, through selection of a high frequency range, suitable for estimating the concentration of a peptide or protein analyte in the surrounding tissue based on the impedance spectrum analysis. Preferred such peptide and protein agents are listed below:

BNP

B-type (or brain) natriuretic peptide (BNP) has in several studies been shown to correlate extremely well with patients' degree of heart failure. If BNP is measured, this would be a terrific HF metric, already well known by the physician community. By measuring BNP on, e.g. a daily basis the physician would be given unprecedented data of the patient's HF status between check-ups. This would mean quicker follow-up times for the physicians as measurements would already have been made and improved care for the patient as the diagnosis could be made on data not only acquired at the day of the follow-up.

ANP

A-type natriuretic peptide (ANP) is similar in structure to BNP. It is released mainly in the heart and the release is increased e.g. during atrial distention or stretching. As the left atrial (LA) pressure increases in HF, measuring ANP would lead to the same advantages as BNP. The present invention can therefore be used for ANP measurements.

Troponin, Myoglobin and Creatine Kinase

When a patient is suspected to suffer from ischemia, blood samples can be taken and analyzed for elevated levels of troponin, myoglobin or creatine kinase. The levels of these are elevated after myocardial damage, e.g. ischemia.

By continually or periodically measuring the presence of these "ischemia markers", the invention can be used for making a diagnosis faster at the hospital. This also has the potential of detecting so-called silent ischemias (non-symptomatic ischemias). This would improve patient care and episode outcome.

The frequency bandwidth utilized by the signal source 120 of the invention is preferably in the range of 10 MHz to 10 GHz. In particular for peptide and protein analytes, the bandwidth is preferably selected to be in the range of from about 100 MHz to about 10 GHz.

It is anticipated by the invention that the signal source 120 could generate a current (voltage) signal of a single selected bandwidth or frequency. This is particular useful if the IMD 100 is mainly utilized for measuring and monitoring a single analyte having an absorbance or resonance frequency in the bandwidth. However, in alternative embodiments, the signal source 120 preferably sweeps over larger frequency ranges by then generating different current (voltage) signals of different frequencies or bandwidths. In such a case, the IMD 100 has the potential of monitoring several different analytes. The frequency sweeping functionality of the signal source 120 also has advantageous implementation aspects even if a single analyte is of interest. The reason could be that the analyte has absorbance and/or resonance tops at different frequencies that are not coverable by the limited bandwidth of a single current (voltage) signal. The signal source 120 can then be arranged for providing a signal train of increasing or decreasing frequencies.

In this embodiment, the IMD 100 has a signal measurer 130 arranged connected to at least two electrodes 202, 204; 212, 214 through the connecting arrangement 110. The measurer 130 is provided for measuring a resulting voltage or current signal sensed or captured by two electrodes 202, 204; 212, 214 and originating from the tissue. This resulting voltage (current) signal is due to the applied current (voltage) signal from the signal source 120. In a preferred implementation, the signal measurer 130 generates a sensed (AC) voltage signal using at least two connected electrodes 202, 204; 212, 214. The sensed signal could be a single composite signal of a given bandwidth or could be a train of signals of varying frequencies.

The signal source 120 and the signal measurer 130 are connected to an impedance determiner 140 provided in the IMD 100 for determining an impedance signal. The determiner 140 utilizes the measured or sensed voltage (current) signal from the measurer 130 together with information of the generated and applied current (voltage) signal from the signal source 120.

The impedance determiner 140 can utilize different filter combinations, such as bandpass filters, in order to obtain multiple different impedance signals based on the measured voltage signal and the applied current signal. In such a case, it is possible to achieve a set of impedance signals at different frequencies of the applied bandwidth and individually process one or more of these signals. Alternatively, a "raw" or only partly filtered impedance signal can be used for the purpose of the present invention.

An impedance vector is generally employed for identifying the electrodes 202, 204; 212, 214 used for signal application and signal sensing, respectively. As is known in the art, bipolar impedance vectors utilize the same two electrodes for both signal application and signal sensing. In tripolar impedance vectors, the current signal is applied to a tissue over two electrodes and is sensed over two electrodes, one of which but not the other was employed for the signal application. Finally, in quadropolar vectors, two dedicated signal applying electrodes are used and two dedicated, different, signal sensing electrodes.

Generally bipolar vectors typically give a more local representation of the tissue impedance in the close vicinity to the electrodes. Correspondingly, tripolar and quadropolar vectors could be advantageous when monitoring an analyte in a tissue present between two medical leads to thereby mainly get an influence of the impedance signal from the intermediate tissue and not other surrounding tissues.

In order to increase the specificity in the measurements of the invention, different impedance vectors can be utilized for monitoring or measuring a single analyte. This can be useful if a particular impedance vector will be marred by large noise or captures other non-desired variations in the impedance signal. For this purpose, the signal source 120 can generate and apply a first current (voltage) signal to a tissue using a first set of two connected electrodes 202, 204. The signal measurer 130 measures the resulting voltage (current) signal from the tissue with the same or different electrodes 202, 204; 212, 214. The signal source 120 could then apply a second current signal, which could be a copy of the first signal, but then over a second set of two connected electrodes 212, 214, of which at least one is different from the electrodes 202, 204 of the first set. The signal measurer 130 once again measures the resulting voltage signal.

In an alternative approach, the signal source 120 applies two following current signals over the same electrode pair 202, 204 but the signal measurer 130 senses the first resulting voltage utilizing a first set of two electrodes 202, 204 and senses the second resulting voltage signal with a second set of two electrodes 212, 214.

The impedance determiner 140 can then calculate two "parallel" impedance signals for the two different impedance vectors. Such a usage of different impedance vectors in the signal measurements can significantly increase the specificity and resolution in the analyte monitoring of the invention.

A signal processor 150 is arranged connected to the impedance determiner 140 for generating an estimate of the concentration of a monitored analyte in the surrounding tissue. The signal processor 150 performs a spectrum analysis of the determined impedance signal by analyzing the amplitude and/or phase at different frequencies. By detecting changes in the amplitude and/or phase at selected frequencies the signal processor 150 is able to register changes in analyte concentration and can even be able to calculate absolute concentration values.

Figure 5:
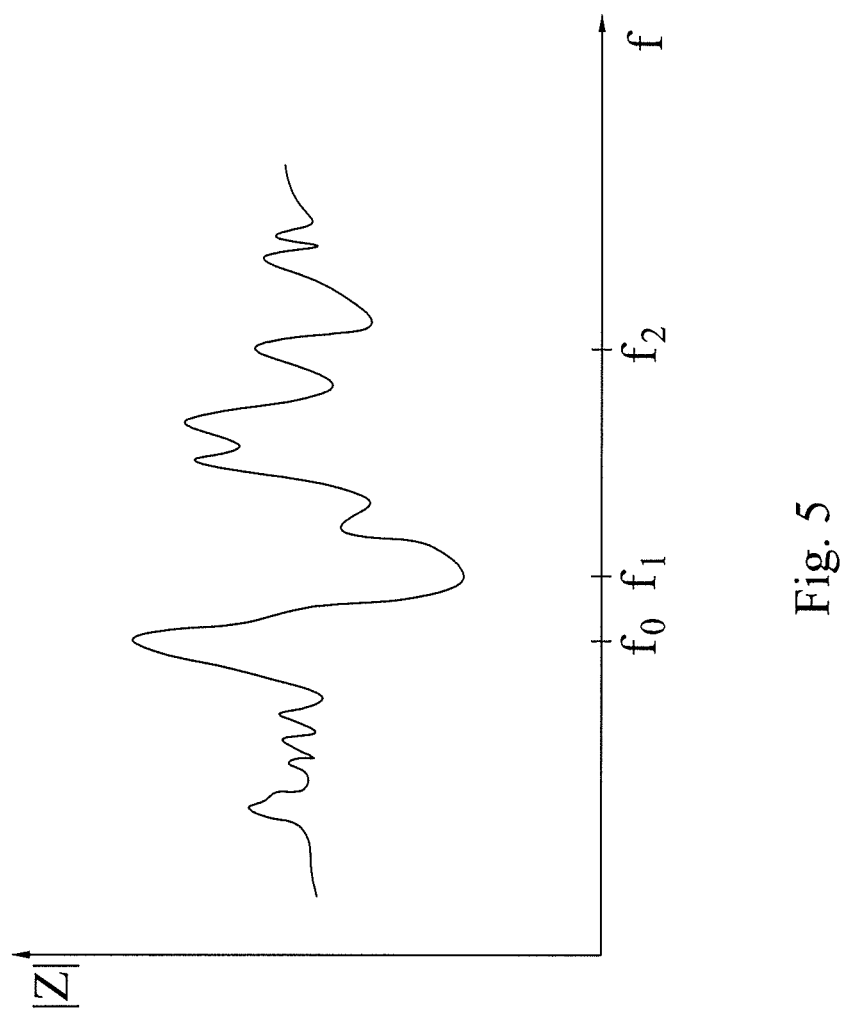
FIG. 5 is a diagram illustrating an impedance spectrum detectable according to the present invention.

With reference to FIG. 5, the spectrum analysis of the processor 130 is preferably performed by investigating the amplitude (phase) of the impedance signal at particular frequencies $f_0$, $f_1$ descriptive of absorbance/resonance events due to the particular analyte. The analysis can be performed by measuring the absolute values at these frequencies $f_0$, $f_1$. However, such an absolute measurement requires sophisticated calibration procedures in order to map these absolute amplitude/phase values into absolute concentration values. In such a case, such a mapping procedure can be performed in a laboratory environment under controlled conditions to get a mapping table or function that allows conversion of measured absolute values into estimates of absolute analyte concentrations. The resulting mapping table or function can then be programmed into the IMD 100 either before implantation or be loaded into the IMD 100 from a programmer (see FIG. 1) after implantation.

Alternatively, the signal processor 150 utilizes a relative absorption/resonance method involving, in addition to the at least one frequency of interest $f_0$, $f_1$, a reference frequency $f_2$. This reference frequency $f_2$ is selected to have an absorbance that is insensitive to, i.e. does not vary with, the concentration of the analyte. In such a case, the signal processor 150 preferably calculates a ratio of the amplitude at frequency of interest $f_0$ or $f_1$ and the reference frequency $f_2$, such as $f_{0,1}/f_2$ or $f_2/f_{0,1}$. The processor 150 then determines an estimate of the analyte concentration based on this ratio.

The estimation of the analyte concentration of the present invention is performed based on a spectrum analysis of an impedance signal. This involves analyzing the complex impedance Z=R+jX, such as the change in amplitude |Z| or phase of the impedance signal. Also other signals obtainable from the impedance signal can be used by the signal processor for the analyte concentration estimation of the invention. Examples of such related impedance signal include the admittance signal Y. As is well known in the art, admittance is the inverse of impedance, i.e.

$$Y = 1/Z = \frac{R}{R^2 + X^2} - j\frac{X}{R^2 + X_2}.$$

A further example include a conductance signal, which is the real part of the reciprocal of the electric impedance, i.e.

$$G = \text{Re}(Y) = \frac{R}{R^2 + X^2}.$$

According to the present invention, estimate of analyte concentration encompasses both an absolute concentration value, such as $mol/dm^3$, g/ml, etc., but also relative concentration representations. Thus, an estimate of analyte concentration also covers a concentration representation specifying an X times increase or decrease in the analyte concentration as compared to a reference value or a previous analyte concentration measurement. For instance, the analyte concentration can be generated based on a comparison of a current spectrum value (amplitude/phase at one or more frequencies or ratio of amplitude/phase at multiple frequencies) and a previously determined spectrum value generated based on a corresponding impedance spectrum analysis by the processor 150 at a previous time instance.

In a particular implementation, the signal processor 150 can perform a co-processing of impedance signals originating from different impedance vectors, as described above. The processor 150 then analyzes the changes in impedance amplitude and/or phase in these signals at selected frequencies. If a significant amplitude change is only present for one of the impedance vectors at one of the interesting frequencies but not in other impedance vectors recorded close in time, that amplitude change can be due to other causes than a change in the analyte concentration. As a consequence, the signal processor 150 can urge the signal source 120 to perform further complementing signal applications or the processor 150 simply discards the current dubious measurements.

The actual frequencies utilized by the signal source 120 could be hard-coded before implantation of the IMD 100. However, the present invention also provides for a flexible adaptive signal solution. For this reason a signal controller 160 is arranged in the IMD 100 connected to the signal source 120. This controller 160 generates, among others, frequency control signals that are employed by the signal source 120 for determining the bandwidth frequencies of the generated current or voltage signal. This means that the signal source 120 is preferably a frequency tunable signal source 120, where the tunability of the signal frequency is controlled by the signal controller 160. The controller 160 can then have access, e.g. in a memory 180, information of desired frequencies for the signal. In a preferred embodiment, this information can be updated through downloading new frequency information data from a non-implantable device, such as the programmer, into the IMD 100. The frequency tunability can therefore be updated even after implantation and during operation of the IMD 100 in a subject body.

The IMD 100 preferably has a memory 180 for storing the determined concentration estimate or representation for later use. The device 100 can then perform new analyte measurements intermittently or periodically and store the different measurement results in the memory 180 for trending purposes. Thus, the IMD 100 then detects any significant changes in the analyte concentration by comparing analyte estimates generated at different time instances to thereby be able to, for instance, diagnose a medical condition associated with an increase or decrease in the analyte concentration. The IMD 100 may also utilize multiple generated concentration estimates for the purpose of calculating an average analyte concentration in the tissue. This average concentration can then be used for diagnostic purposes by comparing a later determined analyte concentration with the average concentration. If there is a significant difference between the concentration estimates, the IMD 100 can store or tag information thereof in the memory 180 for later use. Furthermore, if there is no significance difference between the estimates, the average concentration estimate can be updated based on the newly generated analyte concentration to thereby provide an adaptation in the estimate averaging.

Instead of storing the measurement results in the memory 180 or as a complement thereto, measurement results may be uploaded from the IMD 100 to an external non-implanted device, such as the programmer in FIG. 1. In such a case, a physician will get access to several concentration estimates collected over a time period and can use this information for diagnostic purposes, such as detecting the onset of a medical condition or used in adjusting administration levels of medicaments.

The invention is based on the discovery that the frequency modulation of the transmitted signal depends on intrinsic body activity, such as breathing and cardiac beating. Such activity-dependency can be important for the interpretation of the frequency spectrum of the determined impedance signal. In order to reduce this signal blurring, the IMD 100 preferably synchronize the act of current (voltage) signal application with variations in the intrinsic body activity.

The IMD 100 preferably has an electric signal analyzer 170 connected to at least one electrode-containing medical leads 200; 210 through the connector 110. The signal analyzer 170 processes (intrinsic and paced) electric signals sensed by the electrode(s) 202, 204; 212, 214 of the lead(s) 200; 210 and originating from a body tissue, typically the heart. The analyzer 170 could, for instance, identify, based on the sensed electric signals, the start of a heart cycle, the systole phase of a heart cycle and the diastole phase of a heart cycle. In such a case, the processed electric signal can be regarded as an intracardiac electrogram (IEGM), from which such events can be detected by the signal analyzer 170.

The signal controller 160 is then responsive to the representation of the variation in intrinsic body activity from the signal analyzer 170. This means that the controller 160 generates, based on the input from the analyzer 170, a synchronization signal that is forwarded to the signal source 120 and causes the source 120 to generate and apply a current (voltage) signal to the electrodes 202, 204; 212, 214 on the lead(s) 200; 210. In this way, the signal application becomes synchronized to a particle phase of the intrinsic body activity, such as synchronized with inhalation, exhalation or systole, diastole. This means that for a periodic or regular analyte monitoring based on the impedance spectrum analysis, the current (voltage) signal can be applied at corresponding phases of the intrinsic body activity but still at different time instances.

Alternatively, only selected portions of the impedance signal is utilized by the signal processor 150 in the estimation of the analyte concentration. In such a case, those interesting portions can be identified based on information from the electric signal analyzer 170.

As a further alternative, the impedance determiner 140 or the signal processor 150 can filter away the contribution from such intrinsic body activities such as respiration and heart beating from the impedance signal.

The frequency spectrum is not only depending on intrinsic body activities, such as heart beating and respiration, but also the body posture of the subject can affect the spectrum of the determined impedance signal. As a consequence, the IMD 100 can advantageously be equipped with or be connected to a body posture sensor 175. An example of such body posture sensors includes accelerometers, such as micro-electromechanical system (MEMS) based accelerometers. The sensor 175 can then generate a signal representative of the current body posture of the subject, e.g. by discriminating between standing and lying position or standing, sitting and lying position.

The signal controller 160 is then responsive to this body posture signal and generates based thereon a synchronization signal that is forwarded to the signal source 120. The source 120 generates a current (voltage) signal upon reception of the synchronization signal.

Having this body-posture synchronization capability, the signal controller 160 is able to limit signal application to particular body postures to thereby obtain a consistency and body posture-independency in the impedance signal processing, in particular for regular or periodic signal transmission and analysis.

The units 120 to 170 of the IMD 100 can be implemented in hardware, software of a combination of hardware and software.

Figure 3:
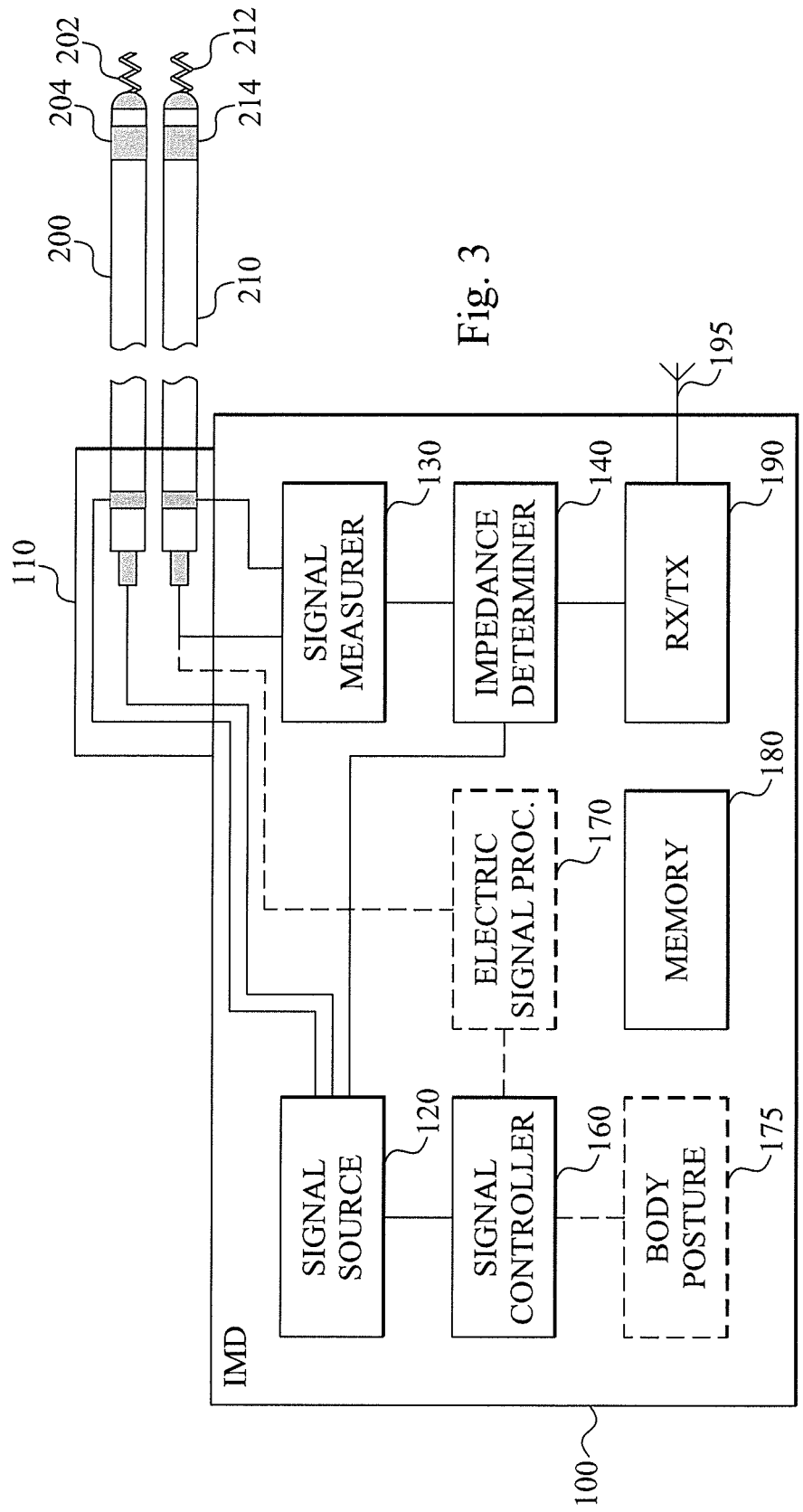
FIG. 3 is a schematic block diagram of another embodiment of an implantable medical device according to the present invention.

FIG. 3 illustrates another embodiment of the IMD 100 according to the present invention. In this embodiment, the IMD 100 does not include the signal processor that performs the processing of the received RF signal in order to generate the estimate or representation of the analyte concentration. The reason for this is that the spectral analysis performed by the processor can sometimes, depending on the particular analyte to monitor, be a quite complex task. In order to save power and thereby increase the operational time of the battery driven IMD 100, the processing can be performed by a non-implanted device that does not have the limited processing capability and limited power supply of the IMD 100. A typical example of such a non-implanted device is illustrated in FIG. 1 represented as the programmer.

The impedance determiner 140 is connected to a transmitter 190 having a transmitting antenna 195 utilized for unidirectional or bidirectional communication with the non-implanted device. It is anticipated by the invention that this antenna 195 can be a RF antenna or an inductive antenna.

The units 120 to 170 and 190 of the IMD 100 can be implemented in hardware, software of a combination of hardware and software.

Figure 4:
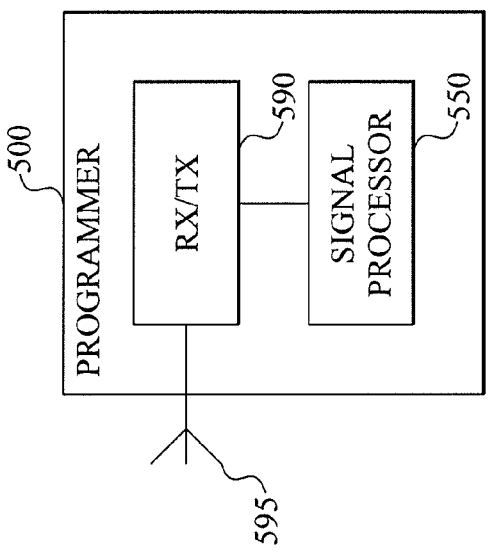
FIG. 4 is a schematic overview of an embodiment of an analyte measuring system according to the present invention.
Figure 4:
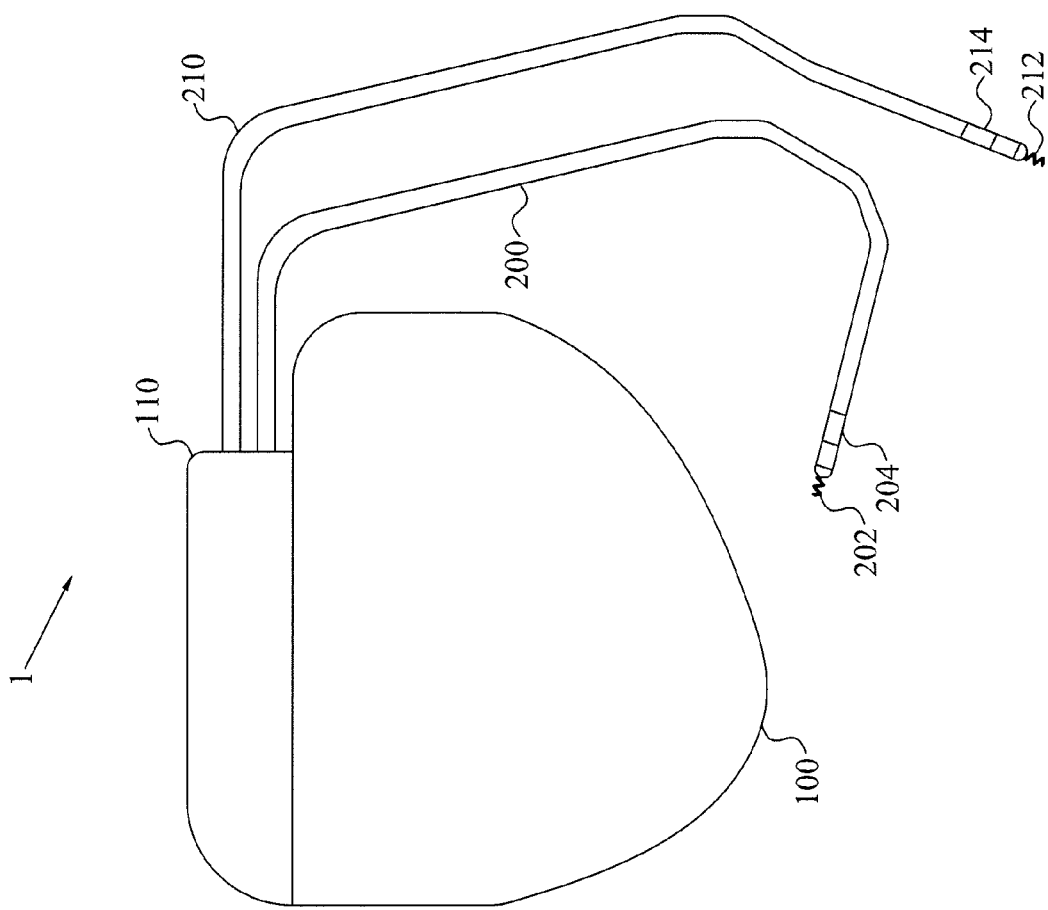

FIG. 4 illustrates an embodiment of the analyte measuring system 1, in which the spectrum analysis of the determined impedance signal is performed by an external, non-implanted device 500. The device 500 has a receiver 590 connected to a receiving antenna 595 for conducting wireless communication with the IMD 100. The antenna 595 and receiver 590, in particular, receives a representation of the impedance signal from the transmitter and transmitting antenna of the IMD 100. The receiver 590 is connected to a signal processor 550 according to the present invention, which performs the previously described spectrum analysis of the received impedance signal.

The analyte measured and monitored according to the present invention is an analyte present in a tissue of a subject body. In a preferred embodiment, the tissue is blood so that the analyte concentration is then the blood concentration. Other preferred tissues include cardiogenic tissue, such as myocardium. As a consequence, the electrodes utilized by the present invention are preferably placed in or in connection with the tissue in which the analyte is to be monitored. However, the advantage of using impedance signals of the present invention is that the electrodes do not necessarily have to be place directly or immediate connection with the measuring tissue. As long as the applied current (voltage) signal is able to penetrate through the tissue and the resulting voltage (current) be captured by the electrodes, thereby achieving a more unrestricted placement of the electrodes.

The impedance signal measurements of the present invention can be used for local analyte measurements, such as when utilizing the electrodes positioned close to the tissue of interest and in particular when utilizing bipolar impedance vectors. The invention can though also perform more global or regional analyte measurements. In the latter case, the electrodes utilized for signal application and sensing, respectively are arranged in spatially different sited in the subject body, such as for tripolar and quadropolar vectors and/or utilizing the IMD can as one of the electrodes.

FIG. 5 is an example of an absorbance spectrum that could be obtained by the analyte measuring system of the present invention. As can be seen from the figure, such an absorbance spectrum will exhibit peaks of a global and local maximums and valleys of a global and local minimums depending on what analytes that are present in a test tissue and in what concentrations the analytes are present. The interesting frequencies ($f_0$, $f_1$) that are relevant for a given analyte and that should be investigated in the spectrum analysis of the invention can be defined in advance based on laboratory tests and/or mathematical estimations of absorbance/resonance frequency based on the three-dimensional structure of the analyte and its constituents.

Figure 6:
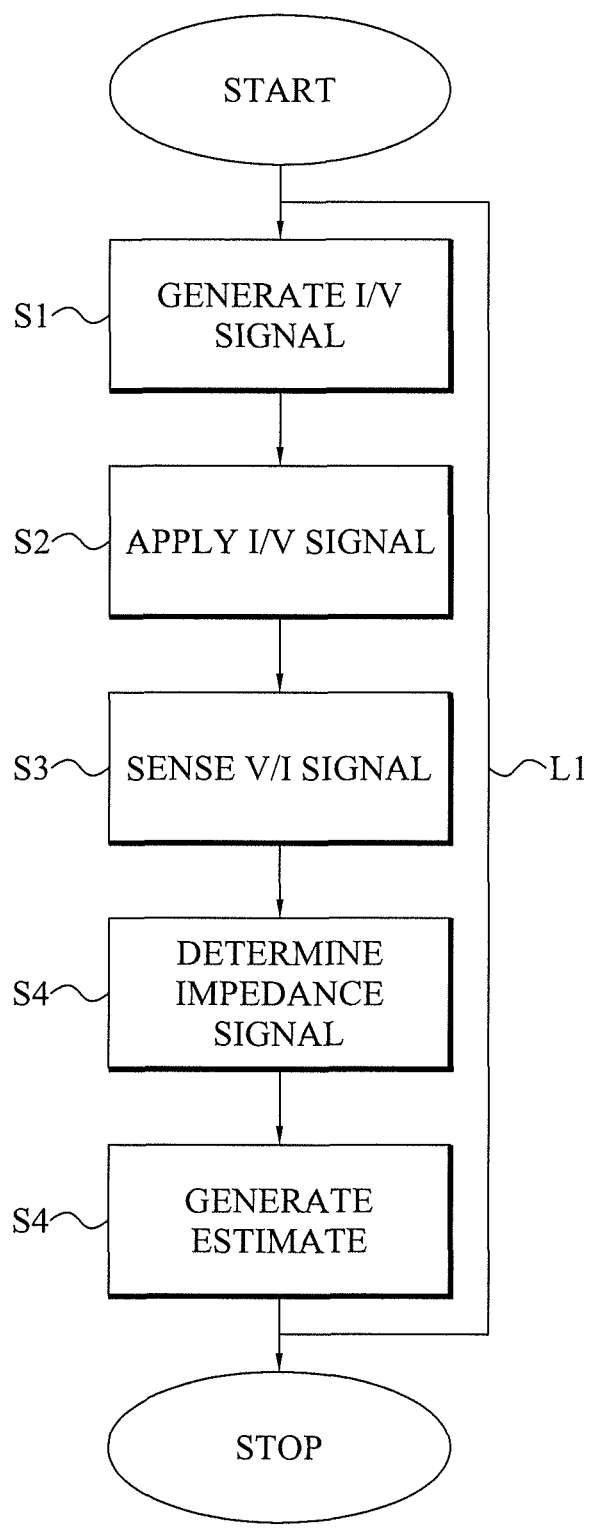
FIG. 6 is a flow diagram of an analyte measuring method according to an embodiment of the present invention.

FIG. 6 is a flow diagram of a method for estimating an analyte according to the present invention. The method starts in step S1, where a current or voltage signal of selected bandwidth is generated by a signal source arranged in an IMD. A next step S2 applies the generated current/voltage signal to a tissue or medium in an animal, preferably mammalian and more preferably human, body utilizing two electrodes connected to the IMD, such as provided on one or two leads connected to the IMD. A resulting voltage/current signal is sensed by two electrodes in step S3, where the electrodes can be the same or different from the signal applying electrodes. Step S4 uses the measured voltage/current signal together with the applied current/voltage signal or information of the applied current/voltage signal (such as frequency, amplitude, phase) for determining an impedance signal. This impedance signal is processed in step S5 through a spectrum analysis to generate an estimate or representation of the concentration of the analyte in the surrounding tissue.

The analyte measurements of steps S1 to S5 are preferably performed at multiple different time instances, such as intermittently or periodically, which is schematically illustrated by the line L1. The time interval between measurements is mainly dependent on the particular analyte to monitor and can non-inventively be selected by a physician. For some analytes, a periodic measurement once every hour or even more often could be advantageous at least during a limited time interval. For other analytes, one or a few measurements per day, week or month could be adequate.

The present invention is not limited to measuring and monitoring a single analyte. In clear contrast, by varying the frequency of the applied current/voltage signal to adapt to absorption and/or resonance frequencies of different analytes, it is actually possible to measure and monitor concentrations and concentration changes of multiple different analytes in a subject body. Furthermore, the periodicity in such measurements can be different for the different analytes.

Although modifications and changes may be suggested by those skilled in the art, it is the intention of the inventors to embody within the patent warranted heron all changes and modifications as reasonably and properly come within the scope of their contribution to the art.

We claim as our invention:

1. An analyte measuring system comprising:
an implantable medical device comprising:
   an electrode connecting arrangement connectable to at least two implantable electrodes;
   a signal source that generates a current or voltage signal and for applying said current or voltage signal to a tissue using said at least two implantable electrodes;
   a signal measurer that measures a resulting voltage or current signal from said tissue sensed by said at least two implantable electrodes;
   an impedance determiner that determines an impedance signal based on said generated current or voltage signal and said measured resulting voltage or current signal; and
   a signal processor that generates an estimate of a concentration of an analyte in said tissue by making a spectral analysis of said impedance signal determined by said impedance determiner;
wherein said signal processor generates said estimate of said analyte concentration based on a ratio of an amplitude of said impedance signal at a first frequency and an amplitude of said impedance signal at a second frequency; and
wherein said signal processor generates said estimate of said analyte concentration based on a comparison of said ratio and a corresponding ratio determined by said signal processor based on a spectral analysis of a reference impedance signal determined based on a previously applied current or voltage signal and a previously measured resulting voltage or current signal.

2. The system according to claim 1, wherein
said signal source generates a composite current or voltage signal having a defined bandwidth covering a frequency range;
said signal measurer measures a resulting composite voltage or current signal from said tissue sensed by said at least two implantable electrodes;
said impedance determiner determines said impedance signal based on said generated composite current or voltage signal and said measured composite resulting voltage or current signal; and
said signal processor generates said estimate of said concentration of said analyte based on an analysis of said impedance signal at multiple selected frequencies in said frequency range obtained by bandpass filtering said impedance signal.

3. The system according to claim 1, wherein said implantable medical device comprises a transmitter with a connected transmitting antenna for transmitting a representation of said impedance signal to a non-implantable device comprising a receiver with a connected receiving antenna that receives said representation, wherein said signal processor is arranged in said non-implantable device.

4. The system according to claim 1, wherein said signal processor is arranged in said implantable medical device.

5. The system according to claim 1, wherein said signal source generates said current or voltage of at least one frequency in a range of 1 MHz to 1 THz.

6. The system according to claim 5, wherein said signal source generates said current or voltage of at least one frequency in a range of 10 MHz to 10 GHz.

7. The system according to claim 6, wherein said signal source generates said current or voltage of at least one frequency in a range of 100 MHz to 10 GHz.

8. The system according to claim 1, wherein said implantable medical device further comprises:
   a signal analyzer generates a representation of a variation in intrinsic body activity based on a sensed electrical signal from a tissue; and
   a signal controller that generates a synchronization signal based on said representation of said variation in intrinsic body activity and forwards said synchronization signal to said signal source, said signal source responding to said synchronization signal and generates said current or voltage signal based on said synchronization signal.

9. The system according to claim 1, wherein said implantable medical device further comprises comprising:
   a body posture sensor that generates a representation of a body posture of a subject in whom said implantable medical device is implanted;
   a signal controller that generates a synchronization signal based on said representation of said body posture and forwarding said synchronization signal to said signal source, said signal source responding to said synchronization signal by generating said current or voltage signal based on said synchronization signal.

10. The system according to claim 1, wherein said implantable medical device is selected from a group consisting of:
a pacemaker;
a cardiac defibrillator; and
a cardioverter.

11. An analyte estimating method comprising:
generating a current or voltage signal;
applying said current or voltage signal to a tissue using two implantable electrodes;
sensing a resulting voltage or current signal from said tissue using two implantable electrodes;
determining an impedance signal based on said generated current or voltage signal and said sensed resulting voltage or current signal; and
generating an estimate of a concentration of an analyte in said tissue by making a spectral analysis of said impedance signal;
wherein said generating an estimate of a concentration further comprises determining a ratio of an amplitude of said impedance signal at a first frequency and an amplitude of said impedance signal at a second frequency and comparing said ratio and a corresponding ratio based on a spectral analysis of a reference impedance signal determined based on a previously applied current or voltage signal and a previously measured resulting voltage or current signal.

* * * * *